United States Patent
Skog et al.

(10) Patent No.: US 10,932,813 B2
(45) Date of Patent: Mar. 2, 2021

(54) MINIMALLY INVASIVE TISSUE HARVESTING DEVICE

(71) Applicants: Mårten Skog, Nässjö (SE); Petter Sivlér, Linköping (SE); Ranjithkumar Ravichandran, Linköping (SE); Johan Junker, Glommen (SE); Daniel Aili, Linköping (SE); Johan Thorfinn, Linköping (SE); Moustafa Mohamed Hussein Elmasry, Linköping (SE); James Harris, Greenwood Village, CO (US)

(72) Inventors: Mårten Skog, Nässjö (SE); Petter Sivlér, Linköping (SE); Ranjithkumar Ravichandran, Linköping (SE); Johan Junker, Glommen (SE); Daniel Aili, Linköping (SE); Johan Thorfinn, Linköping (SE); Moustafa Mohamed Hussein Elmasry, Linköping (SE); James Harris, Greenwood Village, CO (US)

(*) Notice: Subject to any disclaimer, the term of this patent is extended or adjusted under 35 U.S.C. 154(b) by 127 days.

(21) Appl. No.: 16/040,639

(22) Filed: Jul. 20, 2018

(65) Prior Publication Data
US 2018/0325543 A1  Nov. 15, 2018

Related U.S. Application Data

(63) Continuation of application No. PCT/SE2017/050061, filed on Jan. 23, 2017.

(30) Foreign Application Priority Data

Jan. 22, 2016 (SE) ........................ 1650080

(51) Int. Cl.
A61B 17/322 (2006.01)
A61B 17/32 (2006.01)
(Continued)

(52) U.S. Cl.
CPC ...... *A61B 17/322* (2013.01); *A61B 17/32002* (2013.01); *A61B 17/3494* (2013.01);
(Continued)

(58) Field of Classification Search
CPC ............ A61B 17/322; A61B 17/32002; A61B 17/3494; A61B 2017/00969; A61B 2017/320064
See application file for complete search history.

(56) References Cited

U.S. PATENT DOCUMENTS 5,415,182 A  5/1995  Chin et al.
5,591,187 A  1/1997  Dekel
(Continued)

FOREIGN PATENT DOCUMENTS

JP  2009207659 A  9/2009
JP  2014113211 A  6/2014
WO  2014/028626 A1  2/2014

*Primary Examiner* — Ashley L Fishback
(74) *Attorney, Agent, or Firm* — Gabriela B. Tomescu, Esq.; Bergenstråhle & Partners AB

(57) ABSTRACT

A tissue harvesting device (1), comprising a rotary cutting tool (10) adapted to cut soft tissue and a collection container (20) including a central bore (21) extending in a longitudinal direction and with a distal opening (22), wherein the cutting tool is arranged in the central bore of the collection container and adapted to pass through the distal opening and draw harvested soft tissue fragments into the collection container, and a housing (30) accommodating the cutting tool and the collection container, wherein the collection container is axially movable with respect to the housing.

17 Claims, 4 Drawing Sheets

(51) Int. Cl.
*A61B 17/00* (2006.01)
*A61B 17/34* (2006.01)

(52) U.S. Cl.
CPC ............... *A61B 2017/00969* (2013.01); *A61B 2017/320064* (2013.01)

(56) References Cited

U.S. PATENT DOCUMENTS

| | | | | |
|---|---|---|---|---|
| 6,071,284 A | * | 6/2000 | Fox | A61B 10/0233 606/102 |
| 2004/0031770 A1 | * | 2/2004 | Gardner | B65D 1/0246 215/297 |
| 2004/0059254 A1 | | 3/2004 | Pflueger | |
| 2004/0210229 A1 | | 10/2004 | Meller | |
| 2015/0196287 A1 | | 7/2015 | Hatta | |

\* cited by examiner

MINIMALLY INVASIVE TISSUE HARVESTING DEVICE

This application is the continuation of International Application No. PCT/SE2017/050061, filed 23 Jan., 2017, which claims the benefit of Swedish Patent Application No. SE 1650080-3, filed 22 Jan., 2016, the entire contents of which are hereby incorporated by reference.

TECHNICAL FIELD

The present invention relates generally to the field of tissue transplantation, and more specifically, to devices and methods for replacing or regenerating soft tissue by auto-transplantation (autograft), allotransplantation (allograft) or xenotransplantation (xenograft). An autograft is a tissue transplant donated from the same individual, usually from another area of the body to heal injured tissue. An allograft is a tissue transplant from a genetically non-identical donor of the same species, whereas a xenograft is a tissue transplant from a different species. The apparatus of the present invention facilitates the collection of soft tissue fragments from one or more donor sites, e.g. for use in transplantation of micro grafts for wound treatment, such as deeper burns, pressure ulcers etc.

The invention is not limited to use only in wound care and its related uses, but may be used to collect soft tissue fragments from any other site in a human or animal body for use in any other suitable area of the same or another human or animal body. The invention is described below in a non-limiting manner with reference to wound care applications for ease of description and understanding.

BACKGROUND ART

Skin tissue may be subject to many forms of damage, including burns, trauma, depigmentation and the like. Grafts are often used to repair damaged skin when the skin cannot promote self-healing. Indeed, today, skin grafting procedures have become an almost integral part of advanced wound care (e.g., treatment of diabetic ulcers, burns, pressure ulcers etc.). However, grafting techniques generally involve a large amount of tissue being removed from a donor site, preferably from the patient, and/or expensive and complex cultivation procedures using laboratory facilities to form larger portions of graft tissue from smaller donor samples.

Sheet grafts can provide an improved appearance of the repaired tissue site and have been used. For example, sheet grafts may be used on large areas of the face, neck and hands, so that these more visible parts of the body can appear less scarred after healing. A sheet graft may be used to cover an entire damaged region of skin, e.g., if the damaged site is small. Small areas of a sheet graft can be lost after placement because a build-up of fluid (e.g., a hematoma) can occur under the sheet graft following placement of the sheet graft.

Sheet grafts may be full-thickness or split-thickness. A conventional split-thickness graft can be formed, e.g., by harvesting a sheet of epidermis and upper dermal tissue from a donor site, in a procedure similar to that of peeling an apple. The split-thickness graft can then be placed on the location of the burn or ulcer. The skin tissue may then grow back at the donor site following a generally extended healing time. Split-thickness grafts may be preferable to full-thickness grafts because removing large amounts of full-thickness skin tissue from the donor site can lead to scarring and extensive healing times at the donor site, as well as an increased risk of infection.

However, skin tissue removed from the donor site for a split-thickness skin auto graft may include both the epidermis and a portion of the dermis, which can lead to some scarring and/or depigmentation (e.g., hyper-or hypo-pigmentation) at the donor site.

Large areas of skin may be damaged by burns, which generally require removal of larger areas of tissue from donor sites to repair them. A commonly encountered problem in larger wounds (e.g., burns etc.) is lack of healthy skin surfaces, e.g., skin from another part of the patient that is not damaged and can be donated to the wound area.

Traditionally processing of tissue taken from a donor site is used to cover a wound area that is larger than the donor site itself. The ratio of the wound area to the donor site area is called the expansion ratio.

A number of processing methods and strategies to increase the expansion rate are today present. A common method is called meshing, where the surgeon creates a number of small, non-connected cuts in the slice of tissue. The tissue can then be stretched until it has the appearance of a mesh or net. In this state, it can cover a larger area of a wound. Other methods of processing include cutting the tissue into particles with knives, blades, or scissors.

Split thickness skin grafts are often expanded by means of even non-connected cuts in the tissue which allow for the tissue to be stretched in all directions resulting in an even "hole" pattern. This is done partly to allow for a larger wound to be covered and partly to allow for exudates to be removed from the wound instead of being collected under the graft which is a big risk factor for infections. The skin graft can be expanded to varying extent depending on the size of the wound and the amount of available donor sites. The holes that are formed in the mesh are usually healing with the formation of scar tissue which causes a "fish scale" pattern on the patient which is a big part of the problem of aesthetic outcome associated with skin grafting. Frequently the skin grafts fail and have to be removed, and new skin grafts need to be harvested further worsening the extent and aesthetical appearance of both the donor sites and engraftment sites.

There are also some advanced treatments where a biopsy is taken, cells are then isolated and cultured. The cells believed to be keratinocytes is after culturing sprayed over the wound to promote wound healing. Cultured cells are expensive and come with risks and are not always working in a satisfying way. Cultured keratinocytes used for covering of wounds (cultured epithelial autografts) are frequently cultured either directly on tissue culture treated polystyrene plastic flasks or dishes, on coated flasks or dishes or in flasks that contain a layer of cells, frequently referred to as feeder cells or feeder layer cells, that have been treated to prevent them from dividing and only provide signals that promote the survival of the keratinocytes. Feeder layer cells are often of murine origin and compose an inherent risk in the form of transfer of pathogens. Cells cultured on tissue culture treated polystyrene are frequently reported to be devoid of their stem cell subsets as the tissue culture treated polystyrene is thought to stimulate the differentiation of the cells from stem cells or progenitor cells towards adult cells. Furthermore, culturing and expansion of cells is believed to enrich for rapid dividing cells that might have an increased risk of becoming cancerous cells. Indeed, reports have recently been published where patients treated with cultured keratinocytes have needed surgical removal of skin cancers a few years after the grafting of the cultured epithelial autografts.

More lately methods and apparatus have been developed for making donor skin into micro grafts by mincing the graft into pieces less than 1 mm in size. These types of micro grafts have been proven to work for at least 100 times expansion when treating third degree burns on humans. US 2010/0042127 to Elof Eriksson at Brigham and Women's Hospital (Harvard) discloses a skin mincing device for processing harvested dermal tissue to create sub millimetre skin pieces that subsequently may be used to treat burn wounds and diabetic leg ulcers.

US 2010/0145360 discloses a system and method for transplantation of dermal tissue comprising a tissue particle harvester with a tissue cutting tool of a rotating drum, rotating shaft or end mill cutting type. However, this device creates considerable sized wounds at the donor site and also limits the depth at which tissue can be harvested.

Another problem during skin grafting procedures is the creation of new wounds on the donor sites. A study in Linköping, Sweden showed that 40% of the donor sites got problems during the healing. To increase the healing rate most focus has been to look at different types of wound dressings and only a few achievements have been made in the area of alleviating the problems associated with donor sites.

The commercially available product CelluTome™ was developed to make skin grafting easier without inflicting large wounds at the donor site, as disclosed e.g. in US 2012/0035599 and US 2014/0277454. The main principle of the device is that the skin is sucked up through small holes in a plate that is placed on the skin. The suction is applied by means of a vacuum pump. The vacuum is applied for about 1 hour after which the skin parts protruding through the holes are cut off using an integrated blade and the excised skin pieces are subsequently transferred to an adhesive membrane. The membrane is transferred to the site of engraftment and the donor site is covered by a dressing. The main drawbacks with this method is the amount of time required and the size and site limitations of the donor tissue.

SUMMARY OF INVENTION

It is an object of the present invention to overcome the problems encountered by the available prior art as outlined above. In a first aspect of the present invention, there is provided a tissue harvesting device for removing and collecting soft tissue fragments (e.g. micro grafts) from a donor site. The device comprises a rotary cutting tool adapted to cut soft tissue and a collection container for collecting the soft tissue micro grafts produced by the cutting tool. The collection container has a central bore extending in a longitudinal direction and a distal opening. The cutting tool is arranged in the central bore of the collection container and adapted to pass through the distal opening and draw harvested soft tissue fragments into the collection container.

By the rotary motion of the cutting tool, a plurality of soft tissue micro grafts may be harvested and drawn into the collection container. The harvested soft tissue micro grafts collected in the collection container will be in a size and shape ready to be used in subsequent tissue grafting procedures. At the same time, the tissue harvesting device of the present invention minimises the damage caused to the donor site, which reduces the healing time and minimises the creation of new wounds at the donor sites whilst reducing the time needed for the procedure as well as increasing the amount of harvested soft tissue micro grafts compared to known tissue grafting devices. The disclosed device is simple and inexpensive when compared to existing tissue grafting systems and it can be used in a clinical setting not requiring cell cultures, enzymes, or specialised laboratory facilities.

The tissue harvesting device further comprises a housing accommodating the cutting tool and the collection container, wherein the collection container is axially movable with respect to the housing. Axial movement of the collection container with respect to the housing enables proximal displacement of the collection container with respect to the cutting tool, which ensures that the cutting tool can penetrate to the desired depth in the soft tissue to be harvested whilst the distal tip of the collection container will be pressed against and remain in contact with the tissue surface at the intended donor site. Thereby, the harvested soft tissue pieces will be drawn directly into the collection container instead of passing on the outside of the collection container.

The collection container is axially movable in relation to the housing to enable the cutting tool to penetrate into the intended soft tissue while the collection container is in contact with the donor site. If applied to skin, when the device is pressed towards the skin the rotating cutting tool will sever and engage skin fragments to pass through the hollow distal opening into the collection container. Preferably, the cutting tool will be long enough to actively transfer the soft tissue fragments all the way into the collection container. The collected micro grafts can be removed from the collection container and used as micro grafts during the transplantation procedure, e.g. in a hydrogel mixture covered by a primary dressing such as Epiprotect®.

Any type of soft human or animal tissue may be harvested by the tissue harvesting device according to the present invention to be used as soft tissue micro grafts. Examples of soft tissue include, but are not limited to, epithelium (skin, mucosal membranes etc.), connective tissue, muscle tissue and nervous tissue. The tissue harvesting device may be operated substantially parallel or perpendicular to the tissue surface from which soft tissue is to be harvested, or any angle there between.

In an advantageous embodiment, the distal end of the collection container comprises a sharp tip in the shape of a hollow needle. The sharp tip enables the collection container to penetrate the tissue surface through a clean cut to minimise damage to the tissue surface (e.g. epithelium) and to the tissue above the intended target depth. The sharp tip can be of various length depending on the type of soft tissue and required penetration depth. If the soft tissue is skin, the collection container can be used to cut an opening in the epidermis while the cutting tool will work under the "needle", thus protecting soft tissue not intended to be harvested by the cutting tool, and therefore does not increase the wound surface area at the level of epidermis, minimising risk for scarring and infection.

In a further preferred embodiment, the tissue harvesting device further comprises means for selectively fixating the collection container or the cutting tool in relation to one another. By fixing the position of the collection container, the penetration depth of the cutting tool can be controlled and maintained during the harvesting procedure to ensure that only soft tissue from the desired depth is harvested. This will also make it possible to specify a maximal depth, ensuring safety and graft sample quality.

In an advantageous embodiment, the collection container is removably attached to the housing. Preferably, the housing comprises a frangible portion adapted to be broken in order to remove the collection container. By providing a removable collection container, the collected soft tissue grafts may be easily removed from the tissue harvesting device without needing to transfer the soft tissue grafts to a different vessel.

In a preferred embodiment, the tissue harvesting device further comprises a grip connected to a piston arranged coaxially with the collection container and the cutting tool, wherein the piston is adapted to be displaced in a distal direction by longitudinal movement of the grip in relation to the housing and enter the collection container to displace harvested soft tissue fragments towards the distal end of the collection container. Preferably, the distal end of the collection container comprises a frangible portion adapted to be broken by a distal tip of the piston to expose harvested soft tissue fragments. By providing a movable piston to adapted to be displaced distally into the collection container, removal of harvested tissue fragments is facilitated.

In an alternative embodiment, the collection container is cylindrical and equipped with standard syringe connections to enable flushing of the collection container. The collection container may comprise a cylindrical sleeve wherein the distal opening for the cutting tool is arranged in the centre. The syringe connections facilitate removal of the collected soft tissue grafts in that the cylindrical collection container can be flushed.

In a preferred embodiment, the cutting tool is made of a material capable of cutting and severing soft human or animal tissue, e.g. rubber, plastic or silicon, but softer than hard tissue. This enables soft tissue harvesting in the vicinity of hard tissue in the body, such as bone or tooth enamel, without risking damage to the hard tissue.

In an alternative embodiment, the cutting tool is a drill bit comprising spiral flutes adapted to move soft tissue fragments from the donor site into the interior of the collection container. The helical grooves of the spiral flutes work to push the soft tissue pieces proximally into the collection container.

In a further advantageous embodiment, the tissue harvesting device comprises a vacuum source adapted to suck soft tissue fragments into the collection container. The vacuum source provides additional means to draw the harvested soft tissue pieces into the collection container.

In an alternative embodiment, the tissue harvesting device comprises a plurality of cutting tools. Preferably, the collection container comprises a plurality of openings for accommodating the plurality of cutting tools. Alternatively, the tissue harvesting device comprises a plurality of collection containers, each having a respective cutting tool arranged thereon or therein. By providing more than one cutting tool, an increased amount of soft tissue may be harvested in one operation, thereby reducing the time taken and discomfort experienced by the patient. The invention is described below using the alternative with one cutting tool for ease of description and understanding.

In a preferred embodiment, the diameter of the cutting tool is between 0.5 mm and 5 mm. This diameter has been found to be optimal when considering the potential amount of harvested soft tissue compared to the effect and damage caused on the donor site.

An object of the present invention is to provide new method for less invasive soft tissue grafting procedures which enable the operator to collect autologous soft tissue micro grafts ready for direct transplantation without further processing in particular but not limited to, autologous skin grafting procedures such as when treating severe wounds.

The micro grafts can later be removed from the collection container to be used for soft tissue repair.

The tissue harvesting device could be a hand piece that the operator can use with one hand. An electrical motor supported by a battery can drive the rotary movement and the device could be built for either single (disposable) or multiple uses (reusable).

BRIEF DESCRIPTION OF DRAWINGS

The invention is now described, by way of example, with reference to the accompanying drawings, in which.

DESCRIPTION OF EMBODIMENTS

Figure 1:
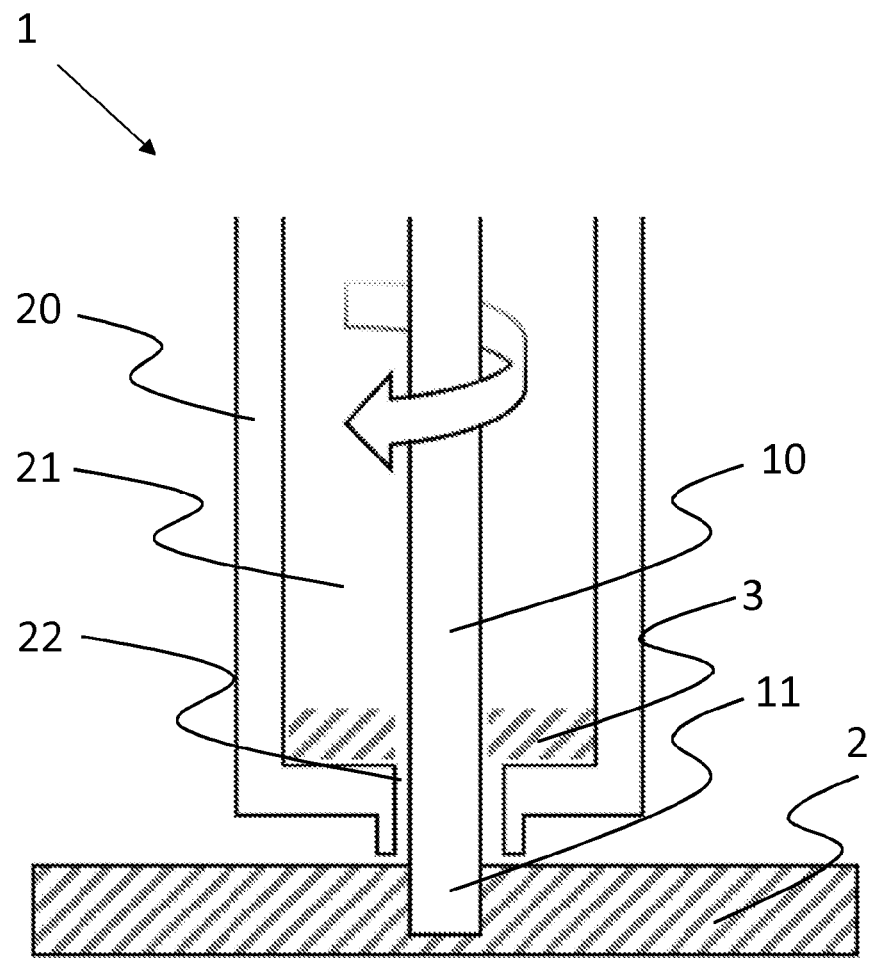
FIG. 1 shows a cross-sectional view of the distal portion of a tissue harvesting device according to the present invention.

In the following, a detailed description of a tissue harvesting device according to the present invention is presented. In the drawing figures, like reference numerals designate identical or corresponding elements throughout the several figures. It will be appreciated that these figures are for illustration only and are not in any way restricting the scope of the invention.

In the context of the present invention, it is understood that the terms "distal" and "distally" refer to a position or direction (furthest) away from the operator when using the tissue harvesting device according to the present invention. Correspondingly, the terms "proximal" and "proximally" refer to a position or direction closest to or towards the operator when using the tissue harvesting device according to the present invention.

In FIG. 1, a schematic cross-sectional view of a tissue harvesting device 1 is shown. Here, only the distal portion intended to make contact with soft tissue is shown. The tissue harvesting device 1 comprises a cutting tool 10 adapted to cut and sever tissue, especially soft tissue as explained above. Furthermore, the tissue harvesting device 1 comprises a collection container 20 including a central bore 21 extending in a longitudinal direction and with a distal opening 22 provided at a distal end. The cutting tool is arranged in the central bore 21 of the collection container 20, preferably such that the axis of rotation of the cutting tool 10 substantially coincides with the central axis of the collection container 20. At least a distal tip or end 11 of the cutting tool 10 is adapted to pass through the distal opening 22 and draw harvested soft tissue proximally into the collection container 20 during the operation of soft tissue harvesting.

The cutting tool 10 may be any suitable rotary tool adapted to cut and remove soft tissue from a donor site, such as e.g. a drill bit with spiral flutes, a milling cutter, a reamer, a burr or similar. The cutting tool 10 is chosen based on the specific type of soft tissue to be harvested, location of donor site, targeted penetration depth and/or desired graft size. Furthermore, the cutting tool 10 may be made of a soft and flexible material, i.e. softer than bone or dental tissue such as enamel and dentin, but harder than the soft tissue intended for harvesting. This enables soft tissue harvesting in the vicinity of hard tissue in the body without risking injury to the hard tissue. The cutting tool 10 preferably has a diameter of between 0.5 and 5 mm, to minimise wound surface area but harvest sufficient amounts of soft tissue micro grafts.

When performing a soft tissue harvesting procedure, the operator places the tissue harvesting device at the desired donor site, e.g. the outer layer of the skin, the epidermis 2. The rotary motion will allow the cutting tool 10 to penetrate the epidermis 2 and cut and remove soft tissue, e.g. in the form of skin fragments 3, from the donor site and transfer the harvested soft tissue fragments 3 proximally into the collection container 20. To this end, the cutting tool 10 may be a drill bit comprising helical or spiral flutes which pull the harvested soft tissue fragments 3 up along the shaft by the rotation of the drill bit. The tissue harvesting device 1 is further provided with or connectable to a power source (not shown) and comprises means for rotating the cutting tool 10 as known in the art, which will not be further discussed here.

Figure 2:
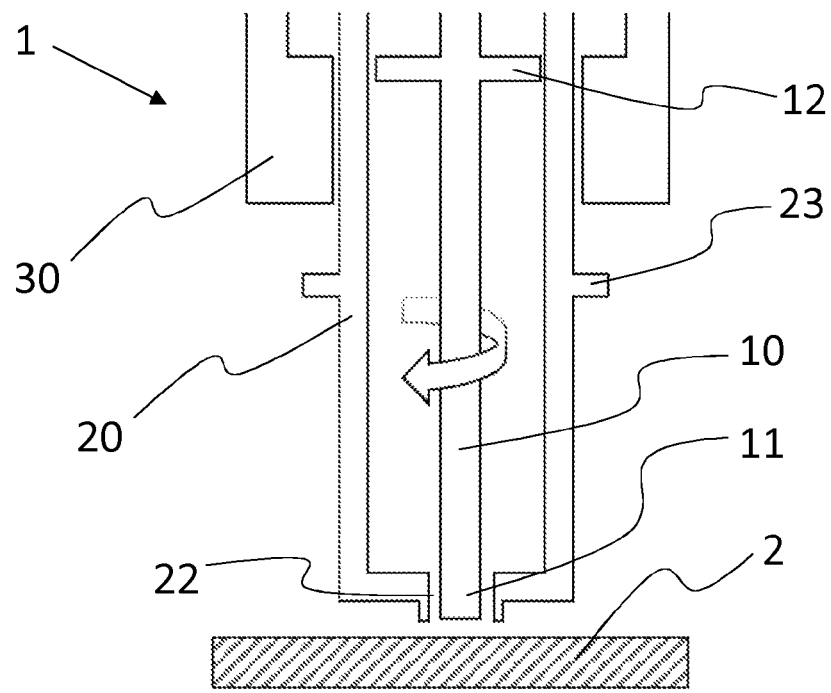
FIG. 2 shows a cross-sectional view of the distal portion of a tissue harvesting device according to a preferred embodiment of the present invention in a retracted, non-exposed state.

In FIG. 2, a tissue harvesting device 1 according to the present invention is shown. The tissue harvesting device 1 comprises a housing 30 in which the rotary cutting tool 10 is mounted with its axis of rotation being substantially parallel with the longitudinal extension of the housing 30. It is also foreseen within the scope of the present invention that the axis of rotation of the cutting tool 10 is arranged at an angle to the longitudinal extension of the housing 30, similar to e.g. a dentist drill. The housing 30 also accommodates the collection container 20, which may have the shape of a cylindrical tube or sleeve with a central bore. Other shapes of the collection container 20 are also contemplated as long as they are suitable for collecting soft tissue harvested by the cutting tool 10. The cutting tool 10 may comprise a centering disc 12 configured to ensure that the cutting tool 10 is centred within the central bore 21 of the collection container 20. The centring disc 12 may also serve to prevent harvested soft tissue fragments from passing towards the proximal end of the collection container 20.

In order to harvest soft tissue from a donor site, the collection container 20 is arranged to be axially movable with respect to the housing 30, e.g. by arranging the collection container 20 to be axially movable inside the housing 30 with the cutting tool 10 being fixed in relation to the housing 30. Additionally, the cutting tool 10 may be axially movable with respect to the housing 30 and the collection container 20. FIG. 2 shows the cutting tool 10 arranged substantially completely inside the collection container 20 in a first, retracted position, wherein the distal tip of the cutting tool 10 does not protrude through the distal opening 22 of the collection container 20. The collection container 20 and/or the cutting tool 10 may be biased towards the first position, e.g. by means of a resilient member such as a spring or similar as known in the art.

Figure 3:
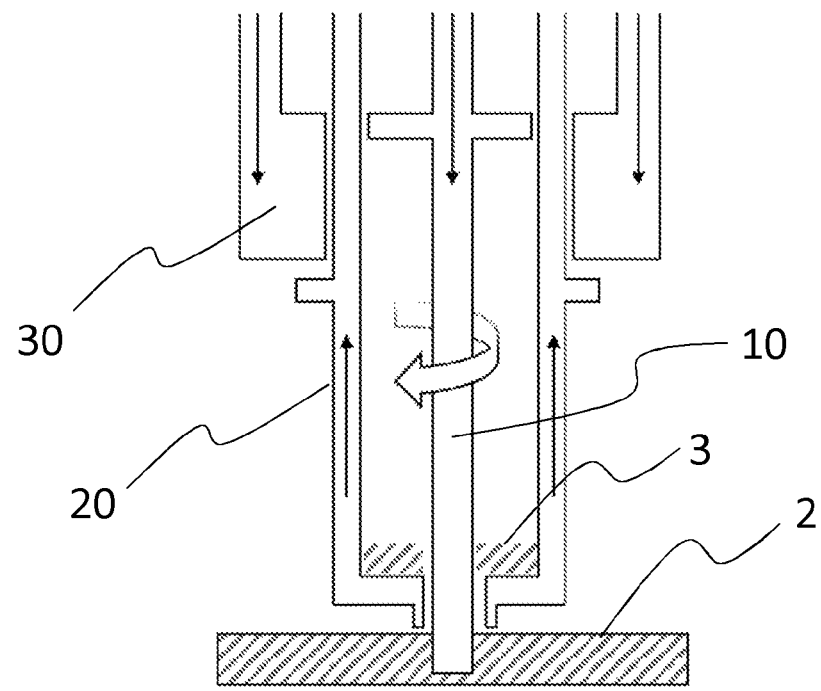
FIG. 3 shows a cross-sectional view of the distal portion of a tissue harvesting device according to a preferred embodiment of the present invention in an extended, exposed state.

FIG. 3 shows the tissue harvesting device 1 of FIG. 2 in operation. The operator has placed the tissue harvesting device 1 on the selected donor site and pressed the tissue harvesting device 1 against the outer layer of the skin, the epidermis 2. This causes the cutting tool 10 and housing 30 to move in a distal direction in relation to the collection container 20, as indicated by the downward arrows, such that the cutting tool 10 protrudes through the distal opening 22 of the collection container 20 and penetrates the skin. At the same time, the collection container 20 remains pressed against the skin and is displaced in a proximal direction in relation to the housing 30 and the cutting tool 10, as indicated by the upward arrows. The rotary motion of the cutting tool 10 will then cut and remove soft tissue from the donor site and transfer the harvested soft tissue proximally into the collection container 20. To this end, the cutting tool 10 may be a drill bit comprising helical flutes which pull the harvested soft tissue micro grafts 3 up along the shaft by the rotation of the drill bit. Because of the tight seal formed by the distal end of the collection container 20 pressed against the skin, the harvested soft tissue fragments 3 will not be spread out from the donor site outside the collection container 20. Instead, the harvested soft tissue fragments 3 will enter into the interior of the collection container 20.

Although described above in relation to skin tissue, the tissue harvesting device 1 according to the present invention may be used to harvest other types of soft tissue such as e.g. soft connective tissue, muscle tissue, nervous tissue, epithelial tissue, mucosal membranes etc. in any part of the body.

The range of axial motion of the collection container 20 determines the depth of penetration of the cutting tool 10 into the soft tissue to be harvested. The outside surface of the collection container 20 may be provided with gradation markings to indicate the penetration depth to the operator. This facilitates harvesting soft tissue at the desired depth. Furthermore, the collection container 20 may be provided with an abutment member, e.g. in the shape of an exterior annular flange 23 arranged to abut against a distally facing portion of the housing 30, in order to limit axial movement in the proximal direction and thus, the penetration depth of the cutting tool 10. Optionally, the tissue harvesting device 1 may be provided with means for selectively fixating the collection container 20 and/or the cutting tool 10 at a desired axial position with respect to the housing 30.

Figure 4:
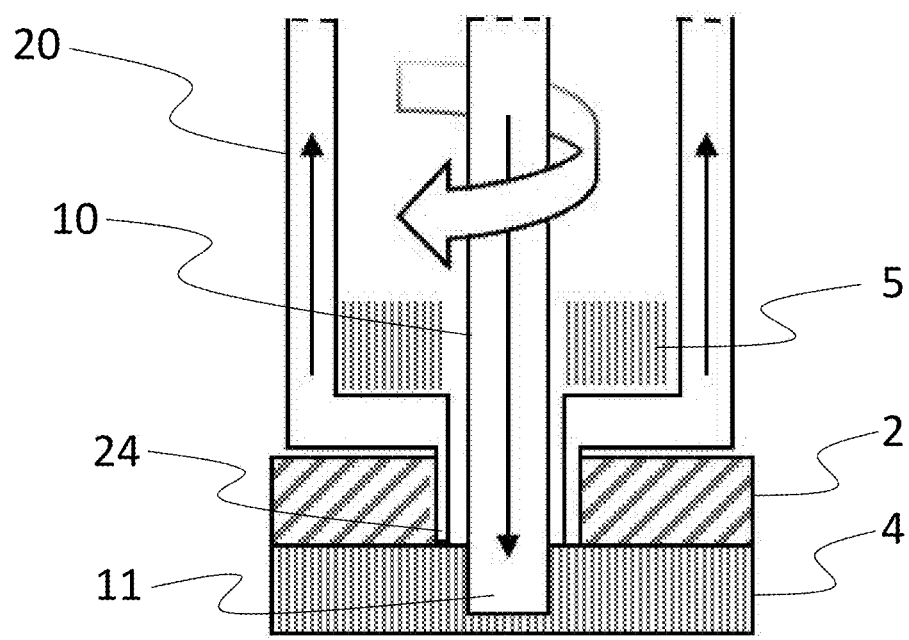
FIG. 4 shows a cross-sectional view of the distal portion of a tissue harvesting device according to an alternative embodiment of the present invention in an extended, exposed state.

FIG. 4 shows a further preferred embodiment of the tissue harvesting device 1 in a close-up view. Here, the distal end of the collection container 20 comprises a sharp tip 24 in the shape of a hollow needle. The sharp tip 24 is adapted to easily penetrate the epidermis 2 at the donor site down to a desired depth, e.g. the dermis 4, and thereby act as a cannula or hollow needle for the cutting tool 10. After penetration, the cutting tool 10 is moved distally through the sharp tip 24 without making contact with the epidermal tissue 2 above the desired penetration depth. This will cause only minimal damage to the epidermal tissue 2 above the intended target depth. At the target depth, the cutting tool 10 will protrude through the hollow needle and harvest the target dermis tissue 4, whereupon the harvested dermis tissue micro grafts 5 will be pulled proximally into the collection container 20 as explained above, whilst minimising the wound surface area at the level of epidermis 2, minimising risk for scarring and infection.

Once a sufficient amount of soft tissue has been harvested, the operator will ease the pressure on the collection container 20 in order to retract the cutting tool 10 through the distal opening 22. In order to remove the harvested soft tissue fragments 3 from the collection container 20, a syringe may be used to flush or withdraw the micro grafts. To this end, the collection container 20 may comprise standard syringe connections (not shown).

As an alternative, the collection container 20 may instead be removably attached to the housing 30 and thus be detached when the harvesting procedure has been terminated. To this end, the housing 30 may comprise a frangible portion adapted to be broken off to allow access to the collection container 20.

Figure 5A:
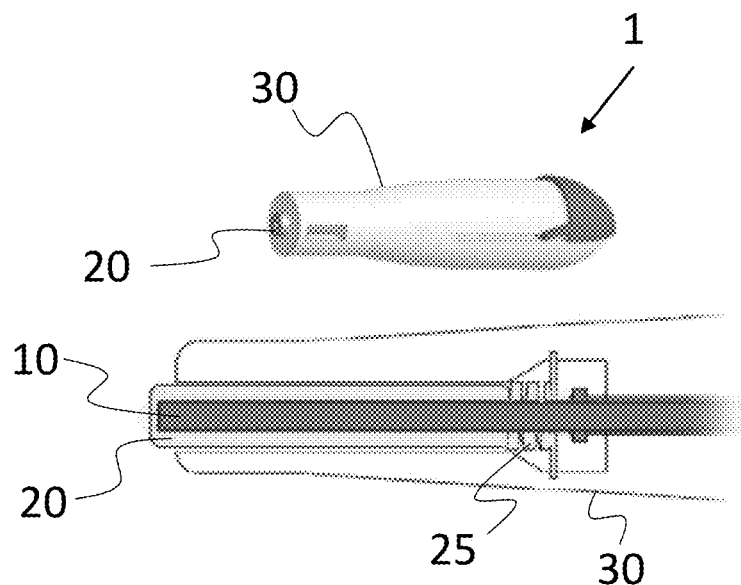
FIGS. 5a-5c show a perspective view and a cross-sectional view of an alternative embodiment of the present invention including a housing in different stages of operation.
Figure 5B:
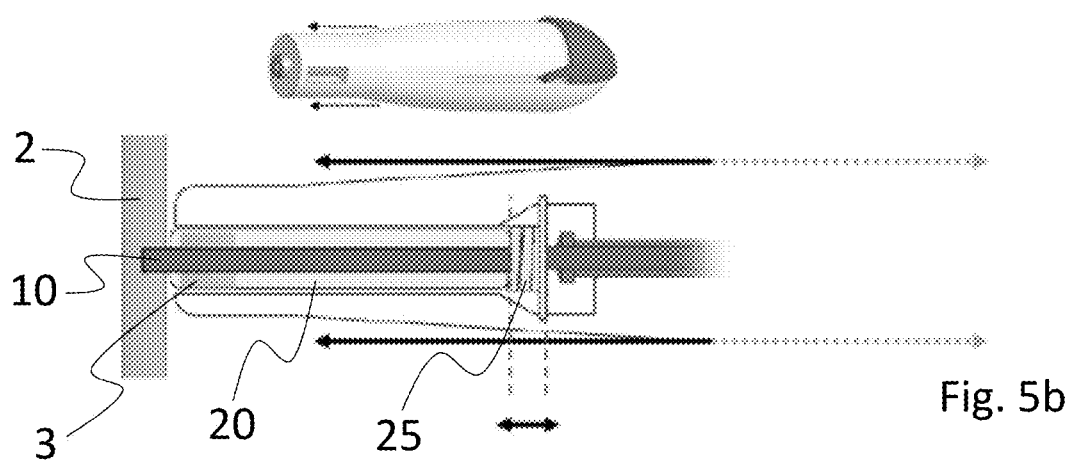
Figure 5C:
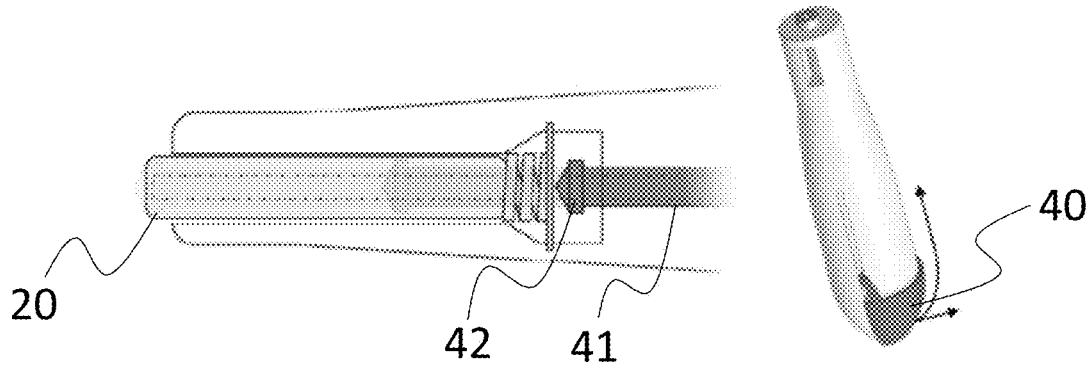

FIGS. 5a-5c illustrate an alternative embodiment of a tissue harvesting device 1 according to the present invention, wherein removal of harvested tissue is further facilitated. As in previous embodiments, the tissue harvesting device comprises a cutting tool 10 arranged in the central bore of a collection container 20 and both being accommodated in a housing 30. As seen in FIG. 5a, the collection container 20 is biased in a distal direction by means of a spring 25, thereby covering the distal tip of the cutting tool 10 in a retracted position. However, other alternatives for biasing the collection container 20 are also foreseen as mentioned above.

In FIG. 5b, the tissue harvesting device 1 is pressed against the surface of the soft tissue to be harvested at the desired donor site as shown by the arrows. As the distal end of the collection container 20 contacts the tissue surface, the force exerted by the operator on the housing 30 causes the spring 25 to be compressed and the collection container 20 to move in a proximal direction in relation to the housing 30 and the cutting tool 10, thus allowing the cutting tool 10 to penetrate into the tissue.

FIG. 5c shows a mechanism for removing harvested tissue from the collection container 20. At a proximal end of the housing 30 there is provided a handle or grip 40 which is connected to a piston 41 arranged coaxially with the collection container 20 and the cutting tool 10. The piston 41 is hollow and the cutting tool 10 is arranged in the central bore of the piston 41, as shown in hatched lines in FIG. 5c. The grip 40 may be rotated with respect to the housing 30 and then moved in a distal direction in relation to the housing 30, thus pushing the piston 41 in a distal direction to enter the collection container 20, as shown in weaker shade in FIG. 5c. Simultaneously, the harvested tissue in the collection container 20 is displaced by the piston 41 in a distal direction and may thus exit through the distal opening 22 of the collection container 20. The diameter of the piston 41 is adapted to the inner diameter of the collection container 20 to achieve a close fit, thus ensuring that all of the harvested tissue is displaced by the piston 41. Advantageously, a hatch or frangible portion at the distal end of the collection chamber 20 is irreversibly opened or broken by the distal tip 42 of the piston 41 as it reaches its distal most position to facilitate removal of harvested tissue. The distal tip 42 may further be sharp to facilitate breaking of the frangible portion. This function also serves to visibly show that the tissue harvesting device 1 and the collection container 20 have been used and should therefore be disposed of.

Also disclosed is a method of harvesting soft tissue micro grafts from a donor site, or creating micro grafts in soft tissue, by means of a rotary cutting tool arranged within a collection container where the soft tissue pieces removed during the procedure will be collected.

The method according to clause 1, where the collection container is cylindrical and equipped with standard syringe connections for easy flushing.

The method according to clause 1, where spiral flutes on the cutting tool is moving the soft tissue fragments into the interior of the collection container.

The method according to clause 1, where the soft tissue fragments is sucked in to the collection container with the help of a vacuum pump.

The method according to clause 1, where number of cutting tools is more than one.

The method according to clause 1, where number of containers is more than one.

The method according to clause 1, where the size of the cutting tool is between 5 mm and 0.05 mm.

The method according to clause 1, where the cutting tool is working parallel to the skin surface.

The method according to clause 1, where the cutting tool is working perpendicular to the skin surface.

Also disclosed is a method of harvesting soft tissue micro grafts from a donor site by a rotating cutting tool equipped with container where the collection container tip is in the shape of a hollow needle providing a clean cut to minimise damage to the tissue surface at the donor site.

The method according to clause 10, where the collection container is cylindrical and equipped with standard syringe connections for easy flushing.

The method according to clause 10, where spiral flutes on the cutting tool is moving the soft tissue fragments into the interior of the collection container.

The method according to clause 10, where the soft tissue fragments are sucked in to the collection container with the help of a vacuum pump.

The method according to clause 10, where number of cutting tools is more than one.

The method according to clause 10, where number of containers is more than one.

The method according to clause 10, where the size of the cutting tool is between 5 mm to 0.05 mm.

The method according to clause 10, where the cutting tool is working parallel to the tissue surface at the donor site.

The method according to clause 10, where the cutting tool is working perpendicular to the tissue surface at the donor site.

The invention claimed is:

1. A tissue harvesting device for harvesting soft tissue from a donor site, comprising:
   a rotary cutting tool,
   a collection container including a central bore extending in a longitudinal direction and with a distal opening, wherein the cutting tool is arranged in the central bore of the collection container and adapted to pass through the distal opening and draw harvested soft tissue fragments into the collection container, and
   a housing accommodating the cutting tool and the collection container, wherein the collection container is axially movable with respect to the housing when the device is in operation;
   wherein the device is formed as a handpiece to be used with one hand, the housing accommodating an electrical motor supported by a battery to drive the rotary movement of the cutting tool, and
   wherein the diameter of the cutting tool is between 0.5 mm and 5 mm and is adapted so as to minimize damage caused to the donor site.

2. The tissue harvesting device according to claim 1, wherein the distal end of the collection container comprises a sharp tip in the shape of a hollow needle.

3. The tissue harvesting device according to claim 1, further comprising means for selectively fixating the collection container or the cutting tool in relation to one another and/or the housing.

4. The tissue harvesting device according to claim 1, wherein the collection container is removably attached to the housing.

5. The tissue harvesting device according to claim 4, wherein the housing comprises a frangible portion adapted to be broken in order to remove the collection container.

6. The tissue harvesting device according to claim 1, further comprising a grip connected to a piston arranged coaxially with the collection container and the cutting tool, wherein the piston is adapted to be displaced in a distal direction by longitudinal movement of the grip in relation to the housing and enter the collection container to displace harvested soft tissue fragments towards the distal end of the collection container.

7. The tissue harvesting device according to claim 6, wherein the distal end of the collection container comprises a frangible portion adapted to be broken by a distal tip of the piston to expose harvested soft tissue fragments.

8. The tissue harvesting device according to claim 1, wherein the collection container is cylindrical and equipped with standard syringe connections to enable flushing of the collection container.

9. The tissue harvesting device according to claim 1, wherein the cutting tool is made of a material which is softer than hard tissue.

10. The minimally invasive tissue harvesting device according to claim 9, wherein the cutting tool is made of rubber, plastic or silicon.

11. The tissue harvesting device according to claim 1, wherein the cutting tool is a drill bit comprising spiral flutes adapted to move soft tissue fragments from the donor site into the interior of the collection container.

12. The tissue harvesting device according to claim 1, further comprising a vacuum source adapted to suck soft tissue fragments into the collection container.

13. The tissue harvesting device according to claim 1, comprising a plurality of cutting tools.

14. The tissue harvesting device according to claim 13, wherein the collection container comprises a plurality of openings for accommodating the plurality of cutting tools.

15. The tissue harvesting device according to claim 13, comprising a plurality of collection containers, each having a respective cutting tool arranged therein.

16. The tissue harvesting device according to claim 1, wherein the tissue harvesting device is disposable.

17. The minimally invasive tissue harvesting device according to claim 1, wherein the collection container is configured to be biased towards a first, retracted position, wherein a distal tip of the cutting tool does not protrude through the distal opening of the collection container, by means of a resilient member.

* * * * *